United States Patent [19]

Khan et al.

[11] Patent Number: 6,066,602
[45] Date of Patent: May 23, 2000

[54] WATERBORNE NON-SILICONE LUBRICANT COMPRISING PHOSPHOLIPID AND POLYETHER

[75] Inventors: Mohammad A. Khan, Sandy; Azhar J. Khan, West Valley, both of Utah

[73] Assignee: Becton Dickinson and Company, Franklin Lakes, N.J.

[21] Appl. No.: 08/907,351

[22] Filed: Aug. 7, 1997

[51] Int. Cl.[7] ................... C10M 173/02; C10M 173/00; C10M 137/04; C10M 145/34
[52] U.S. Cl. .......................... 508/436; 508/307; 508/429; 508/448
[58] Field of Search .................................. 508/436, 307, 508/429, 448

[56] References Cited

U.S. PATENT DOCUMENTS

| | | | |
|---|---|---|---|
| 3,574,673 | 4/1971 | Schweiger | 117/132 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,770,874 | 9/1988 | Allison et al. | 424/88 |
| 4,904,433 | 2/1990 | Williamitis | 264/130 |
| 4,960,814 | 10/1990 | Wu et al. | 524/312 |
| 5,024,947 | 6/1991 | Inlow et al. | 435/240.31 |
| 5,025,004 | 6/1991 | Wu et al. | 514/165 |
| 5,185,006 | 2/1993 | Williamitis et al. | 604/265 |
| 5,589,120 | 12/1996 | Khan et al. | 264/130 |
| 5,653,695 | 8/1997 | Hopkins et al. | 604/265 |
| 5,688,747 | 11/1997 | Khan et al. | 508/208 |
| 5,824,359 | 10/1998 | Khan et al. | 427/2.3 |

FOREIGN PATENT DOCUMENTS

| | | |
|---|---|---|
| 0 318 081 A1 | 5/1989 | European Pat. Off. . |
| 0 733 372 A2 | 9/1996 | European Pat. Off. . |
| 0 778 337 | 6/1997 | European Pat. Off. . |
| 53-145888 | 12/1978 | Japan . |
| WO 96/26997 | 9/1996 | WIPO . |

*Primary Examiner*—Jerry D. Johnson
*Attorney, Agent, or Firm*—Scott S. Servilla, Esq.; Eric M. Lee, Esq.

[57] ABSTRACT

The lubricant of this invention is a combination of a PLURONIC® polyol and a phospholipid. The lubricant is applied to the surface to be lubricated by forming a solution of water and the lubricant. This solution may also include Vitamin E or its derivative. In addition, a solution stabilizer and an antimicrobial agent may be used to clarify the solution and to inhibit microbial growth in the solution.

6 Claims, 1 Drawing Sheet

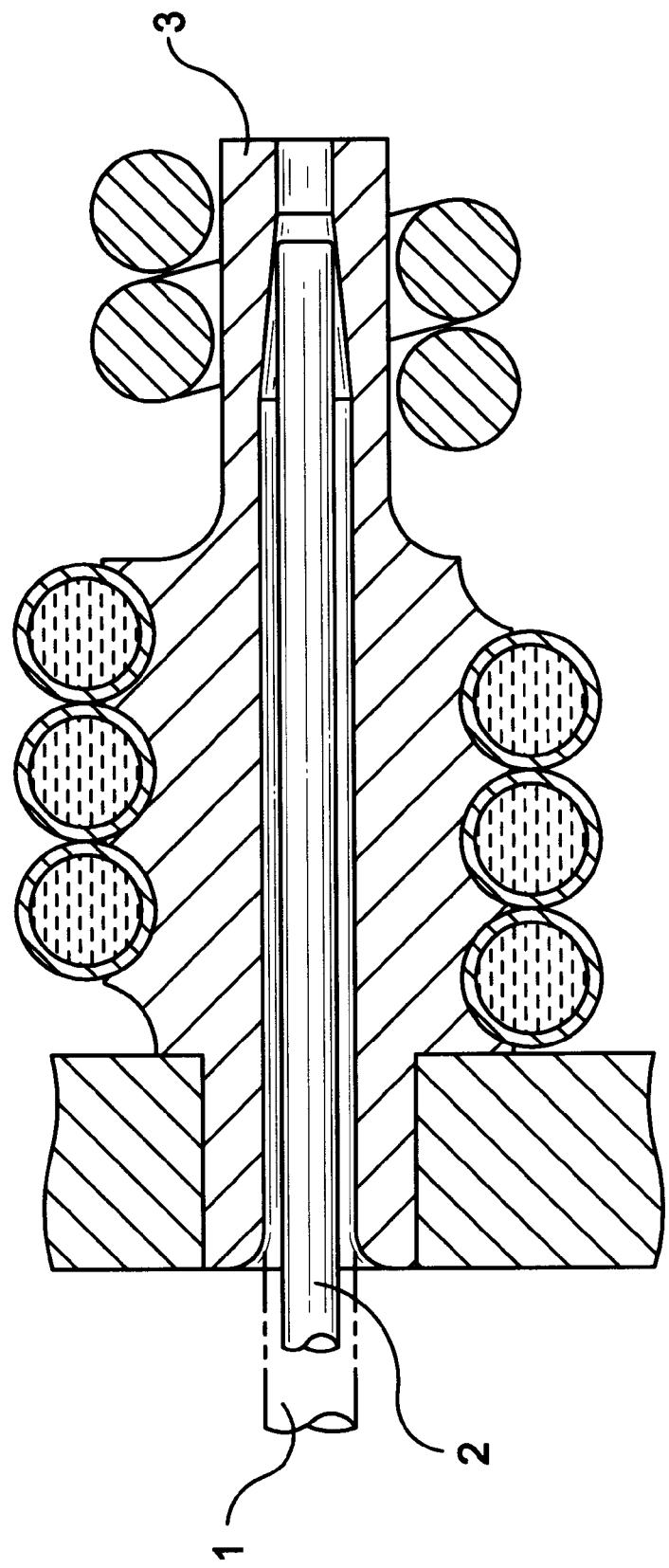

WATERBORNE NON-SILICONE LUBRICANT COMPRISING PHOSPHOLIPID AND POLYETHER

BACKGROUND OF THE INVENTION

This invention relates in general to a lubricant used during the manufacture of intravenous (IV) catheters. In addition, this invention relates to a lubricant solution that facilitates application of the lubricant to a surface and that uses water as the carrier or solvent.

IV catheters are designed to infuse normal intravenous solutions, including antibiotics and other drugs, into a patient. These catheters are also used to withdraw blood from the patient for normal blood-gas analysis as well as other blood work.

The typical catheter is hollow and is extruded out of suitable plastic material such as Teflon, polyvinyl chloride, polyethylene, polyurethane or polyether urethane. In order to insert a catheter into a patient, an introducer needle is used. The needle is typically formed from stainless steel and is hollow. Its distal tip is ground to a sharp tip for easy insertion into the patient. The catheter is initially located coaxially around the introducer needle in an "over the needle" arrangement. The internal diameter of the catheter tip is slightly less than the outer diameter of the needle so that the catheter tip has an interference fit on the needle. The interference fit is necessary so that when the catheter and introducer needle assembly is taken out of the package, the catheter remains snugly on the needle and does not easily slip off. This interference fit also facilitates insertion of the catheter and introducer needle assembly into the patient's vein because it minimizes the chance that the catheter tip will fold over or peel back on the needle tip.

Placement of the catheter and introducer needle assembly into the patient causes sharp pain to the patient. In order to facilitate insertion of the assembly into the vein and to minimize patient discomfort, the shape of the catheter tip is formed so as to produce minimal trauma to the patient during insertion of the catheter into the patient and while the catheter is in place in the patient. Such a preferred tip shape that provides these characteristics has a tapered outer wall and an angled tip and disclosed in U.S. Pat. No. 4,588,398. A process for making that catheter tip, known as the tipping process, is disclosed in U.S. Pat. No. 4,661,300. In this tipping process, the catheter blank is placed on a mandrel. A die having an interior molding surface, which is tapered according to the tip desired on the catheter, is aligned axially with the mandrel. The tip of the catheter blank is heated, typically using RF energy, so that it is flowable. The mandrel and die are brought together so the distal edge of the mandrel engages the tapered portion of the die. This action cleanly forms a smooth and uniform tapered tip for the catheter.

After the catheter is tipped, it must be free of defects such as incomplete formation, substantial flash or jagged edges. The tip must also look smooth and be free of roll-overs. In addition, the length of the catheter must remain within a desired specification after the tipping process. Visual or microscopic examination may be used to determine if there are any tip defects and if the length of the catheter is within specifications. Typically a lubricant is used to allow the tipped catheter to be easily removed from the mandrel and die. If a lubricant is not used, the tipped catheter could stick to the mandrel or die resulting in a deformed catheter when it is removed from the mandrel or die.

Standard tipping lubricants include polydimethyl siloxanes such as Dow Corning DC 360 or curable silicones such as Dow Corning 44159 MDX which are amine terminated and moisture curable. Non-curable amine terminated polydimethyl siloxanes have also been used for this purpose. Such lubricants are described in, for example, U.S. Pat. Nos. 3,574,673; 4,664,657; 4,904,433; and 5,185,006.

An additional mechanism that is used to facilitate insertion of the catheter and introducer needle assembly into the patient is lubrication. Typically the catheter will be lubricated to minimize drag between the catheter and the patient's skin. In addition, lubricant can be applied to the needle to minimize adhesion between the catheter and the needle to facilitate removal of the needle from the catheter. Such catheter and needle lubricants include the same type of lubricants that have heretofore been used during the tipping process.

The amount of lubricant needed to provide lubricity to the catheter, between the catheter and the needle and between the catheter blank and the mandrel and die during the tipping process is very small. Thus in order to control the application of the lubricant, the surface to be lubricated is coated with a lubricant solution that contains the lubricant and a carrier or solvent. Use of a lubricant solution also facilitates application of the lubricant to the inside surface as well as outside surface of the catheter. After the lubricant solution is applied to the surface, the carrier or solvent evaporates leaving the lubricant behind on the surface of the catheter. The silicone oils used as typical lubricants are hydrophobic. Therefore, these compounds must be dissolved in organic solvents in order to prepare a lubricant solution which can be applied to the surface to be lubricated before the tipping process can begin. The primary solvent that has been used heretofore is freon because it is nonflammable and evaporates quickly. Unfortunately, because of recent concerns that chlorofluorocarbons (CFC) react with and destroy the earth's protective ozone layer, the production and use of CFC will cease in the near future. Thus other solvents must be used. Other organic solvents, such as alcohols and hydrocarbons, are highly flammable. Thus, it is too dangerous to use large amounts of these solvents in the tipping process.

SUMMARY OF THE INVENTION

It is therefore an object of this invention to provide a lubricant that does not require the use of a CFC as the solvent or the carrier.

It is another object of this invention to provide a lubricant solution that is "environmentally friendly".

It is still another object of this invention to provide a lubricant solution that is not flammable.

The lubricant of this invention is a pluronic polyol in combination with certain synthetic phospholipids. PLURONIC® polyols are a class of compounds chemically known as poly (oxyethylene) poly (oxypropylene) condensates. Phospholipids are a class of synthetic compounds containing quaternary nitrogen and the phosphotidyl group. Since the PLURONIC® polyol and phospholipid are water soluble, water is used as the carrier to form the lubricant solution. The solution is placed on the surfaces to be lubricated by dipping, brushing or spraying. Upon evaporation of the water, the PLURONIC® polyol and phospholipid remain behind to provide lubricity. The tipping process of this invention requires that the tip portion of the catheter blank be dipped in the lubricant solution or to otherwise have this lubricant solution applied to the surfaces to be lubricated such as by brushing or spraying the lubricant solution onto such surfaces. Once the water evaporates, the catheter blank is mounted on a mandrel and heated. A die and the mandrel are brought into engagement to form the catheter tip. The tipped catheter is then easily and quickly removed from the die and the mandrel.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which:

FIG. 1 is a cross-sectional view of a portion of a die and mandrel arrangement with a catheter blank thereon with the mandrel engaged with the die to form the catheter tip.

DETAILED DESCRIPTION OF THE INVENTION

Although this invention is described in terms of its application to the tipping of IV catheters, it is to be understood that this invention could be used on various medical devices and in processes where a lubricious surface is desirable. For example, this invention can be used to lubricate a catheter and introducer needle to facilitate insertion thereof into a patient.

The lubricant of this invention is a PLURONIC® polyol in combination with certain synthetic phospholipids. PLURONIC® polyols are a class of compounds chemically known as poly (oxyethylene) poly (oxypropylene) condensates. PLURONIC® products are available from the BASF Corporation in Mount Olive, N.J. Specifically, PLURONIC® polyols with molecular weights in the range of about 5000 to about 7000 may be used. Preferably pluronic P123 is used. The chemical formula of these compounds is represented as:

$$HO(CH_2CH_2O)_a(CH_3CHCH_2O)_b(CH_2CH_2O)_cH$$

where $a=13–52$, $b=35–67$, and $c=13–52$.
Preferably between about 1% by weight and about 30% by weight of the pluronic polyol is used in the lubricant solution.

Phospholipids are a class of synthetic compounds containing quaternary nitrogen and the phosphotidyl group. The chemical structure is represented:

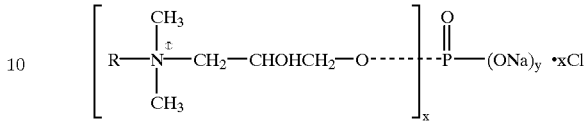

R=fatty acid radical and X+Y=3

The other compounds tested were glycerox HE, chemically known as PEG-7 glyceryl cocoate and glycerox 767, chemically known as polyoxyethylene glyceryl monocaprylate/caprate. Preferably between about 1% by weight and about 30% by weight of the phospholipid is used in the lubricant solution.

Vitamin E is chemically known as alpha-tocopherol and is an antioxidant. Since vitamin E is an antioxidant it prevents degradation of the lubricant solution through oxidation and thus minimizes the effects of aging. In addition, vitamin E and its derivatives, including vitamin E acetate and vitamin E succinate, enhance the lubricity of the lubricant of this invention. Preferably between 0. 1% and 1% by weight of vitamin E or its derivatives is used. The molecular structure of vitamin E is shown below:

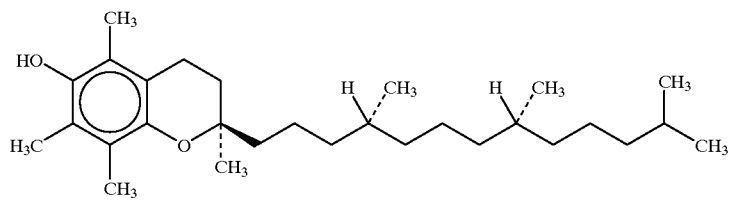

Cosmocil, chemically known as polyhexamethylene biguanide hydrochloride, is an excellent solution stabilizer and antimicrobial agent which inhibits microbial growth in the water based lubricant solution or on the coated surface of the device. Preferably between about 1% and about 5% by weight of cosmocil is used. Another solution stabilizer that can be used is a quaternary ammonium salt. When this is used anti-microbial agents should be included. Examples of anti-microbial agents are: iodophors; phenols; phenolic compounds such as para-chloro-meta-xylenol; and other biguanides such as chlorhexidine gluconate. Even where cosmocil is used, these anti-microbial agents may still be used in the solution. However, cosmocil is preferably used alone because it is less toxic than the other anti-microbial agents. Its molecular structure is shown below:

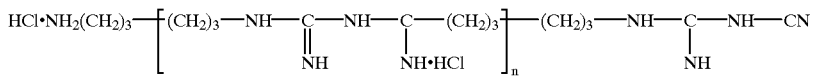

After the lubricant solution is applied to the surface to be lubricated, i.e. the catheter blank, the catheter blank 1 to be tipped is mounted onto a mandrel 2 supported on a carriage (not shown). A die 3 having an interior molding surface, with at least one portion of which is tapered according to the tip desired on the finished catheter, is aligned axially with the mandrel 2. The carriage is moved toward the die 3 such that the end of the catheter blank 1 to be tipped engages the interior molding surface. The carriage is halted at a point after the catheter blank 1 has engaged the tapered portions of the interior molding surface of the die 3, and is biased toward the die 3 with only sufficient force to cause the catheter blank 1 to move further into the die as the catheter blank 1 is heated by RF energy to its melting point and begins to flow. See FIG. 1. The catheter blank 1 is then allowed to heat in the die 3 and is moved into the die 3 as it begins to melt and flow under the biasing force. The mandrel 2 is positioned so that its distal corner is against the tapered portion of the die 3, thus cleanly forming the leading edge of the catheter. The die 3 and catheter therein are then cooled, and the carriage is reversed such that the catheter may be withdrawn from the die 3. Finally, the catheter is removed from the mandrel 2. There is no flash left on the leading edge because of the contact between mandrel 2 and die 3.

EXAMPLE NO. 1

A water solution of each of the compounds was prepared by stirring a known amount of the compound in water with a magnetic stirrer. After sufficient stirring, a clear solution was obtained. 20 ga. Insyte® catheters were tipped using these solutions.

|  | Composition Nos. | | | | | | | |
|---|---|---|---|---|---|---|---|---|
| Ingredients | 1 | 2 | 3 | 4 | 5 | 6 | 7 | 8 |
| PLURONIC ® 123 | 4 | 8 | — | — | — | — | — | — |
| Phospholipid PTC | — | — | 4 | 8 | — | — | — | — |
| Glycerox 767 | — | — | — | — | 4 | 8 | — | — |
| Glycerox HE | — | — | — | — | — | — | 4 | 8 |
| Water | 96 | 92 | 96 | 92 | 96 | 92 | 96 | 92 |

All percentages are described as weight in grams per hundred grams of solution.

None of the solutions were found to produce consistently good quality tips. After the catheters were tipped, it was determined that the tips stuck to the mandrel. The tips usually rolled inward and would produce a hump on the taper. In some cases the tip itself was burnt because the lubrication was not enough to release the tip from the tipping die and mandrel.

EXAMPLE NO. 2

A design experiment was conducted to determine if mixing the phospholipid PTC (chemically known as cocamidopropyl phosphotidyl PG-diamonium chloride) with PLURONIC® P123 and dissolving the two together in water, would produce sufficient lubrication to the catheter for the tipping process. The following are the compositions that were used in the evaluation of the tipping lubricant.

|  | Composition Nos. | | | | | | | | |
|---|---|---|---|---|---|---|---|---|---|
| Ingredients | 1 | 2 | 3 | 4 | 5 | 6 | 7 | 8 | 9 |
| PLURONIC ® 123 | 5 | 4 | 4 | 3 | 3 | 5 | 5 | 3 | 4 |
| Phospholipid PTC | 3 | 3 | 4 | 4 | 3 | 4 | 4 | 4 | 4 |
| Water | 92 | 93 | 92 | 93 | 94 | 91 | 91 | 93 | 92 |

All percentages are described as weights in grams per hundred grams of solution. All three ingredients were mixed together and stirred until a clear solution was obtained. These solutions were then used to lubricate the catheter tip for molding the tip in the catheter tipping machine.

Sixty catheters were tipped using the above compositions as a lubricant. The results are described below:

| Composition No. | Slight hump Taper | Tip Sticking To Mandrel | Rugged Tip | Tip Rolled Inwards |
|---|---|---|---|---|
| 1 | 7 | 2 | 1 | 0 |
| 2 | 3 | 1 | 1 | 0 |
| 3 | 1 | 0 | 0 | 0 |
| 4 | 1 | 0 | 0 | 0 |
| 5 | 2 | 1 | 0 | 0 |
| 6 | 1 | 1 | 0 | 1 |
| 7 | 1 | 2 | 0 | 0 |
| 8 | 1 | 2 | 0 | 1 |
| 9 | 2 | 0 | 0 | 0 |

The figures indicate the number of defective tips found out of a sample size of 60 These results indicate that the combination of a PLURONIC® polyol and a phospholipid provide sufficient lubrication to the catheter for molding a good tip.

The tipped catheters were then lubricated with the solutions. Similarly, the stainless steel cannula needed for 20 ga. Insyte® catheters was also lubricated separately. The catheter was then assembled over the cannula to have a completed catheter-cannula assembly used on patients. The performance of the product was tested as follows:

1. Tip Adhesion: The needle was pulled out of the catheter at a withdrawal rate of 1 inch per minute, and the force was measured. A high measured force would indicate high tip adhesion and poor lubrication.
2. The catheter-cannula assembly was penetrated through 13 mils ±0.5 mils thick natural latex at a penetration speed of 1 inch per minute. The forces generated by the cannula tip, catheter tip and the catheter surface drag were measured. A low force would mean higher lubricity provided by the compositions.

The test results are tabulated below. Products were tested after dipping and aging at 60° C. for 24 hours.

| Composition | Cannula Tip Force (g) | Catheter Tip Force (g) | Catheter Drag (g) | Tip Adhesion (g) |
| --- | --- | --- | --- | --- |
| 1 | 23.4(3.3) | 17.4(2.3) | 4.4(0.6) | 199.5(33.4) |
| 2 | 23.2(4.1) | 15.6(2.4) | 4.2(0.6) | 202.8(31.1) |
| 3 | 24.6(3.9) | 16.9(2.1) | 5.0(0.8) | 199.9(29.0) |
| 4 | 25.9(2.9) | 17.7(2.3) | 4.9(0.7) | 188.0(28.4) |
| 5 | 24.3(3.0) | 18.2(2.3) | 4.5(0.5) | 213.6(39.0) |
| 6 | 24.3(3.1) | 17.4(1.9) | 4.4(0.8) | 175.3(27.7) |
| 7 | 27.8(4.2) | 18.5(1.9) | 4.8(0.6) | 179.3(23.7) |
| 8 | 22.1(2.6) | 16.4(2.4) | 4.7(0.5) | 211.2(34.8) |
| 9 | 23.8(3.2) | 16.3(1.8) | 4.3(0.5) | 189.1(27.1) |

NOTE: ( ) = Standard Deviation
Sample Size = 10
All products were non-sterile

The above test data indicates that all solutions provide adequate lubricity to the needle as well as to the catheter surfaces.

It is surprising to note that the individual ingredients when used alone in water solutions were ineffective to provide molding lubricity for tipping the catheters. However, a combination of PLURONIC® P123 and Phospholipid PTC in certain ratios in a water solution was able to serve as a tipping lubricant and produce an acceptable tip on the catheter.

EXAMPLE NO. 3

A control experiment was run using an Insyte® 22 ga. catheter tubing and a standard silicone based lubrication system. The composition of the current lubrication system is given below:

| Ingredients | Tipping Lube | Catheter Lube | Needle Lube |
| --- | --- | --- | --- |
| Aminomodified Silicone PS-513 | 0.65 | — | — |
| Silicone 1MM CSTK | — | — | 3.0 |
| DC360, 12500 CSTK Silicone | — | 2.5 | — |
| HCFC | 99.35 | 97.5 | 97.0 |

All percentages are described as weights in grams per 100 grams of solution. The silicones were dissolved in hydrochlorofluoro carbon (HCFC-121) until a clear solution was obtained. Sixty catheters were tipped Out of the sixty catheters, the quality of three tips was not acceptable.

The tipped catheters were assembled by lubricating the catheter and the needle separately and sliding the catheter tube over the needle. The catheter-cannula assembly was then tested for tip adhesion and penetrated through natural latex 13 mils ±0.5 mils thick. The results are tabulated below. Products were tested after dipping and aging at 60° C. for 24 hours.

Tip Adhesion (g)=67.8 (1.06)
Cannula Tip Force (g)=23.6 (6.2)
Catheter Tip Force (g)=14.3 (1.8)
Catheter Drag (g)=3.3 (1.7)
Note: ( )=Standard deviation
  Sample Size=10
  All products were non-sterile These results show that the lubricant solution can also be used to provide acceptable lubricity to the catheter and to the needle.

EXAMPLE NO. 4

An additional test was conducted to determine the amounts of the pluronic polyol and phospholipid that should be used to provide an adequate lubrication system. The compositions tested are tabulated below.

| Ingredients | Composition Nos. | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| PLURONIC® P123 | 7 | 10 | 1 | 4 | 4 | 4 | 4 | 4 | 20 | 30 |
| Phospholipid PTC | 4 | 4 | 4 | 7 | 10 | 1 | 20 | 30 | 4 | 4 |
| Water | 89 | 86 | 95 | 89 | 86 | 95 | 76 | 66 | 76 | 66 |

All percentages are given in grams per 100 grams of the solution. Composition Nos. 9 and 10 were highly viscous and thus were not used in the subsequent test. All three ingredients were mixed together and stirred until a homogeneous solution was obtained. These solutions were clear and were used to lubricate the catheter tip to form the tip on the catheter tipping machine.

Thirty 20 gauge Insyte® catheters were tipped using these solutions. The results are listed below.

| Composition No. | Slight Hump Taper | Tip Sticking to Mandrel | Rugged Tip | Tip Rolled Inward |
| --- | --- | --- | --- | --- |
| 1 | 1 | 1 | 0 | 0 |
| 2 | 1 | 0 | 0 | 0 |
| 3 | 2 | 1 | 0 | 0 |
| 4 | 1 | 0 | 0 | 0 |
| 5 | 0 | 1 | 0 | 0 |
| 6 | 2 | 2 | 0 | 0 |
| 7 | 0 | 1 | 0 | 0 |
| 8 | 0 | 0 | 0 | 0 |

These results indicate that the compositions having low percentages of the pluronic polyol and the phospholipid produce acceptable results. Furthermore, higher concentrations of either ingredient can be successfully employed in the tipping process.

Thus, it is seen that a new tipping lubricant is provided that does not require the use of CFC as a solvent and is thus "environmentally friendly." The lubricant solution is also non-flammable.

We claim:

1. A lubricant solution consisting essentially of:
   between about 1% and about 30% of a poly (oxyethylene) poly (oxypropylene) condensates;
   between 1% and about 30% of a phospholipid; and
   the balance water.

2. The lubricant solution of claim 1 further including vitamin E or derivatives thereof.

3. The lubricant solution of claim 2 further including a solution stabilizer.

4. The lubricant solution of claim 3 wherein the solution stabilizer is selected from the group consisting of a quaternary ammonium salt or polyhexamethylene biguanide hydrochloride.

5. The lubricant solution of claim 4 further including an antimicrobial agent.

6. A lubricant consisting essentially of poly (oxyethylene) poly (oxypropylene) condensates and a phospholipid and further including vitamin E or derivatives thereof.

* * * * *